United States Patent
Nic

[19]

[11] Patent Number: 6,113,618
[45] Date of Patent: Sep. 5, 2000

[54] SURGICAL SAW WITH SPRING-LOADED, LOW-NOISE CUTTING BLADE

[75] Inventor: David M. Nic, Vicksburg, Mich.

[73] Assignee: Stryker Corporation, Kalamazoo, Mich.

[21] Appl. No.: 09/229,620

[22] Filed: Jan. 13, 1999

[51] Int. Cl.⁷ .................................................. A61B 17/14
[52] U.S. Cl. .......................... 606/176; 606/82; 606/171; 30/351; D24/146
[58] Field of Search ............................. 606/176, 82, 171, 606/178, 79; D24/146; 30/166.3, 330, 338, 339

[56] References Cited

U.S. PATENT DOCUMENTS

| | | |
|---|---|---|
| D. 337,160 | 7/1993 | Evans . |
| D. 360,946 | 8/1995 | Goris . |
| D. 361,029 | 8/1995 | Goris . |
| 1,940,855 | 12/1933 | Friedman . |
| 3,703,036 | 11/1972 | Karubian . |
| 3,905,105 | 9/1975 | Tuke . |
| 4,020,555 | 5/1977 | Hedrick . |
| 4,233,737 | 11/1980 | Poehlmann . |
| 4,511,334 | 4/1985 | Grafelmann . |
| 5,263,972 | 11/1993 | Evans et al. . |
| 5,382,249 | 1/1995 | Fletcher . |
| 5,433,457 | 7/1995 | Wright . |
| 5,489,285 | 2/1996 | Goris . |

*Primary Examiner*—Michael Buiz
*Assistant Examiner*—Anthony S. King

[57] ABSTRACT

A saw blade (12) for use with a surgical saw (10). The surgical saw has a head (18) that is driven in a oscillating motion in order to cause like motion in the saw blade. The saw blade has a base (22) that is dimensioned to be inserted into a slot (24) in the front of the saw head. The base has a width less than the width of the slot to facilitate the easy insertion/removal of the saw blade. The saw blade also has a main section (36) formed integrally with the base (22) that has the cutting surface of the blade. The saw blade is further formed to have springs (42) that extend from the sides of the base. When the blade is inserted in the slot (24), the springs abut the interior walls (25) of the head that define the slot. A gap (48) separates each leaf spring from the adjacent side of the base. The gaps are dimensioned so that, when inertial motion causes the blade base to move towards a leaf spring, the adjacent gap is never closed, Thus, the reciprocal actuation of the saw blade of this invention does not result in the constant metal-to-metal contact between the saw head and the blade that can produce noticeable amounts of noise.

23 Claims, 4 Drawing Sheets

SURGICAL SAW WITH SPRING-LOADED, LOW-NOISE CUTTING BLADE

FIELD OF THE INVENTION

The invention relates generally to powered surgical tools that include saw blades. More particularly, this invention relates to a powered surgical tool and complementary saw blade that, when actuated, produce relatively little noise.

BACKGROUND OF THE INVENTION

The powered saw is an important powered tool that a surgeon employs in order to perform certain surgical procedures. A typical powered saw has a handpiece in which is housed either an electrically or pneumatically driven motor. The motor is attached, through a drive shaft, to a head, also part of the handpiece. The head is adapted to removably receive a saw blade. The actuation of the motor causes movement of the head and the attached saw blade. This movement of the saw blade is what gives the blade the power to cut through the tissue it is employed to separate. Powered surgical saws are able to cut through both hard and soft tissue much faster, and with greater accuracy, than the manually operated saws that they have replaced. Also, it should be clear that the physical effort a surgeon has to employ to operate a powered surgical saw is much less than that used when cutting tissue with manual saws.

Many surgical saws are designed to be used with flat saw blades. Typically, this type of saw blade has a base that is designed to seat in a complementary slot or opening formed in the head. The saw base has one or more openings or slots in which coupling members integral with the head seat in order to lock the blade to the head. Extending from the base, the saw blade has a main body. The leading edge of the main body is formed with teeth that perform the actual cutting action.

Many surgical saws are designed so that their heads and complementary blades engage in a repetitive right-left-right-left oscillating motion. More specifically, the head of an oscillating motion saw moves in either a sagittal pattern or in oscillatory pattern. When a blade is moved sagittally, it pivots in a plane that is parallel to the axis of the handpiece. When a blade is moved in an oscillating pattern, it pivots back-and-forth in a plane that is angled to the longitudinal axis of the handpiece.

Over the past few years, it has become popular to provide powered surgical saws with heads that have tooless mechanisms for coupling the saw blades to the saws. These mechanisms often have some sort of spring loaded device for holding the head coupling members in position so that they lock the saw blade in place. The coupling member is displaced from the locked state to the release state by the depression of a button also built into the saw head. One advantage of these assemblies is that they make replacing saw blades, which often occurs during surgery, a relatively simply task. All one has to do is depress the button in order to move the coupling member to the unlocked state; the surgical personnel then remove one blade and insert a new blade. Still another advantage of these assemblies is that they eliminate the need to bring another tool, either a small wrench or a key, into the surgical suite. The elimination of this tool eliminates the need to have to sterilize it before an operation and the need to have to account for its presence.

While current surgical saws, with their tooless heads, have proven to be useful surgical tools, there is a disadvantage associated with their use. When an oscillating motion saw with this type of head is actuated, it generates a significant amount of noise. This is because current saw blades do not tightly fit into the saw head slots in which they seat. There are two reasons for this. First, these saw heads and their complementary blades are inherently dimensioned so that there is a small interstitial gap between the blade and the adjacent walls of the saw head that define the complementary slot. This gap is necessary to ensure that the base of the saw can be quickly slide into and removed from the slot. Secondly, there is a slight gap due to the inherent manufacturing impressions that develop during the fabricating of these components. Consequently, each time a saw head changes its direction of motion, the inertial movement of the saw blade, which is still travelling in the first direction, causes the side of the blade to abut against the adjacent surface of the saw head. Each time this motion occurs, noise is produced. These saw blades typically oscillate back-and-forth at a rate of 10,000 to 20,000 cycles/min. The cumulative noise produced by the saw blade repetitively striking the interior walls of the saw head in which it is seated is quite noticeable.

There have been some attempts to provide saw head-and-blade assemblies designed to minimize the noise produced when these components are actuated. In one such assembly, the saw head is provided with outwardly tapered pins and the base of the saw blade is provided with holes in which the pins seat. This arrangement is intended to provide a tight fit between the pins and the adjacent section of the saw blade through which the pins seat. By providing this tight fit, the post-insertion play of the saw blade is reduced. The reduction in this play reduces the incidence of the blade striking the interior walls of the saw head and the noise generated by such action. This assembly has served to minimize the noise associated with the actuation of a surgical saw. However, there are several limitations associated with this assembly. It is costly to precision machine the tapered pins used to hold the saw blade in the head. Moreover, these pins, are subject to wear and can wear at an uneven rate. Over time, as a result of this uneven wear, the saw blade may unevenly seat on the pins. This uneven seating can cause a deformation of the planar alignment of the blade and its teeth. Also, over time, the wear can cause the blades to seat lower and lower on the pins. This can make removal of the blade difficult.

SUMMARY OF THE INVENTION

This invention is related to a new and useful surgical saw-and-saw blade assembly for reducing the amount of noise generated when the saw is actuated. The saw blade of this invention is formed with integral springs. When the saw blade is seated in the head of the saw with which the blade is used, an interference fit is established between the springs and the adjacent surfaces of the saw head. These springs inhibit the metal-to-metal contact that occurs when the saw is actuated so as to substantially eliminate the noise such contact generates.

BRIEF DESCRIPTION OF THE DRAWINGS

The invention is pointed out with particularity in the claims. The above and further advantages of the invention may be better understood by reference to the following detailed description of a preferred embodiment of the invention when taken in conjunction with the accompanying drawings, in which:

DETAILED DESCRIPTION

Figure 1:
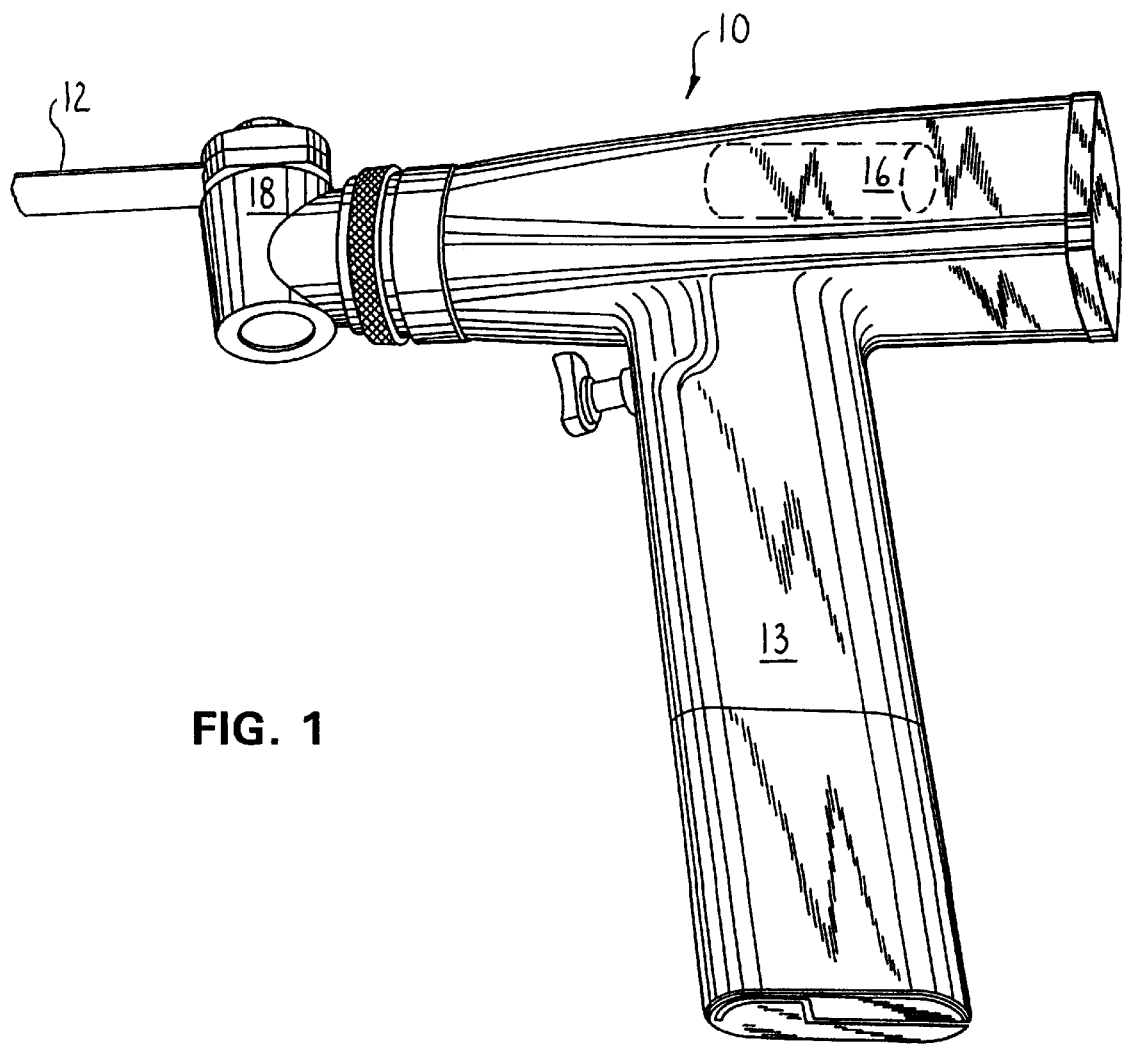
FIG. 1 is a perspective view of a surgical saw with the saw head-and-blade assembly of this invention.

FIG. 1 depicts a surgical saw 10 to which a saw blade 12 is attached. Surgical saw 10 includes a handpiece 13 in which a motor 16 (represented in phantom) is mounted. A head 18 is mounted to the front of the handpiece 13 for receiving the saw blade 12. In the depicted version of the invention, saw 10 is a sagittal saw. The head 18 is constructed to oscillate back-and-forth around a pivot axis that extends perpendicularly relative to the longitudinal axis that extends from the head to the rear end of the handpiece 12. Head 18 is also capable of indexing, rotating, relative to the longitudinal axis of the handpiece. The indexing function of the head 18 makes it possible for the surgeon to selectively orient the saw blade 12 relative to the handpiece so that it is a conveniently located in order to position the blade against the tissue to be cut. One such surgical saw that performs these functions is the Model No. 4108 manufactured by Stryker Instruments of Kalamazoo, Mich.

Figure 2:
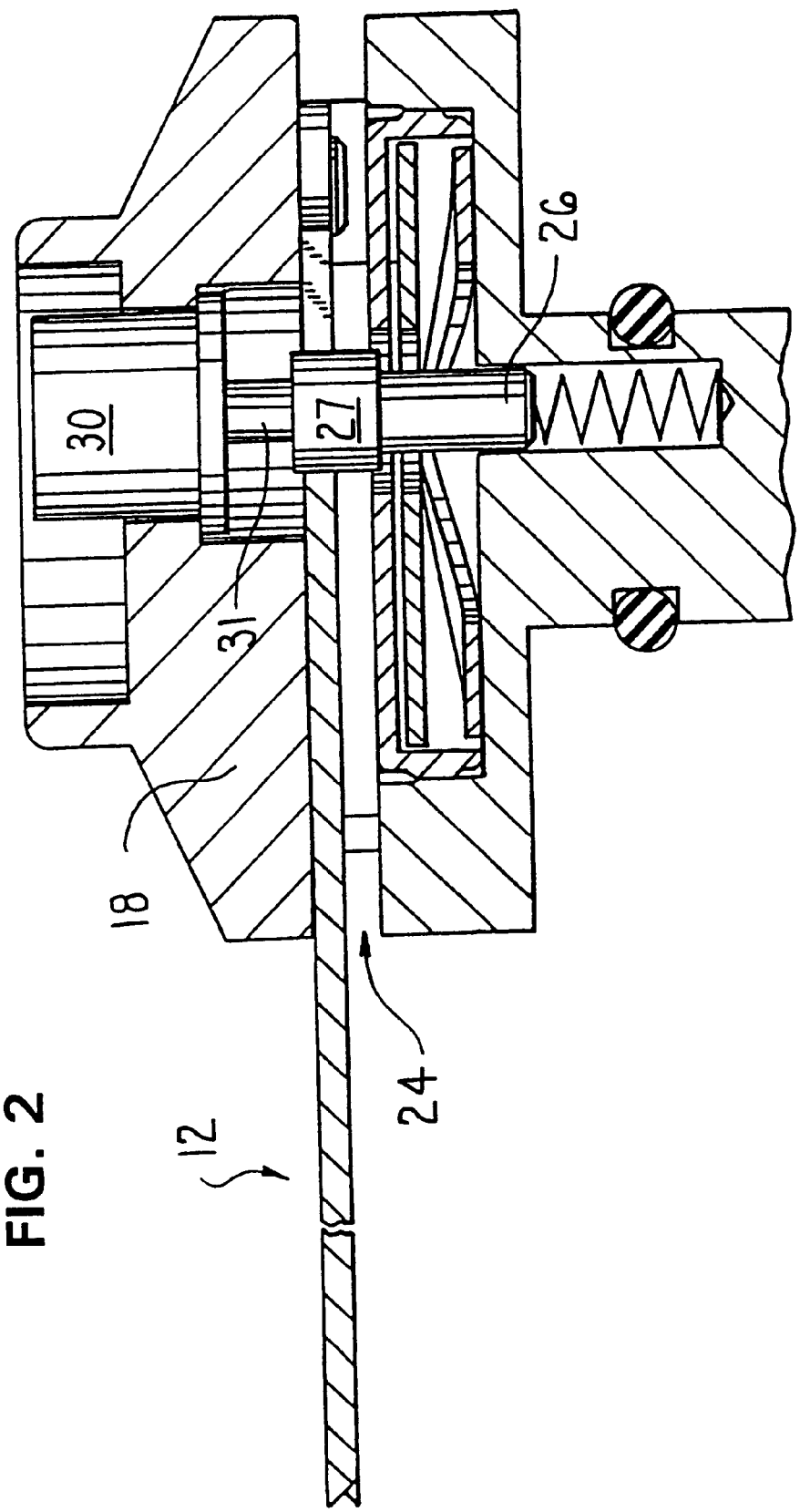
FIG. 2 is a cross sectional view of the head of the saw depicting how the blade is locked in the head.
Figure 3:
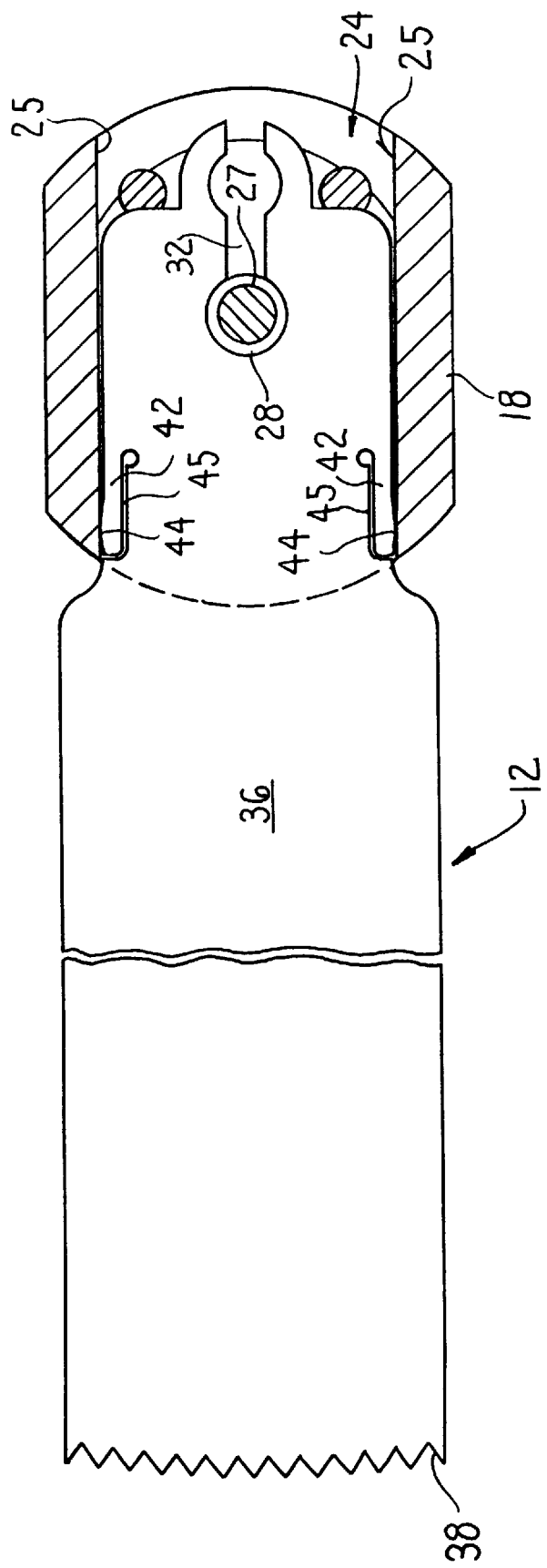
FIG. 3 is a top view depicting how the saw blade seats in the blade head.
Figure 4:
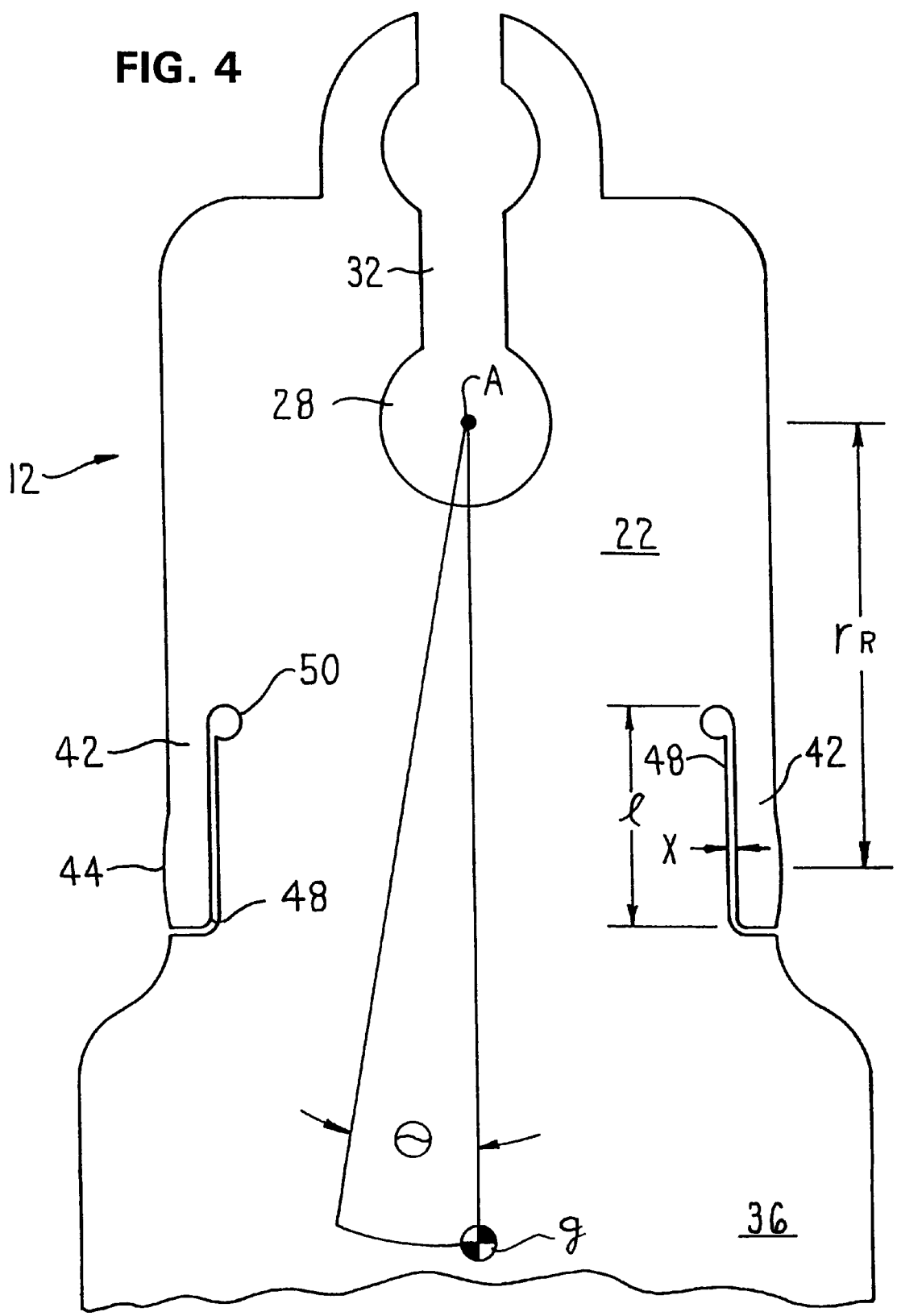
FIG. 4 is a top view of a surgical saw blade of this invention.

As depicted by FIG. 2, 3 and 4 saw blade 12 includes a relatively narrow width base 22 that seats in a forward opening slot 24 formed in the head 18. More particularly, the head has parallel, spaced apart interior side walls 25 that define slot 24. The head 18 is also provided with a multi-section lock pin 26. Lock pin 26 has a large diameter main section 27 that normally seats in a through hole 28 formed in the center of saw blade base 22 to hold the saw blade to the head 18. When one wants to remove the saw blade 12, all that is necessary is to push a release button 30 which forms the head of lock pin 26. The displacement of the release button 30 results in a like displacement of lock pin 26. As a consequence of the displacement of the lock pin 26, a narrow diameter portion 31 of the pin aligns itself with the saw blade 12. This portion of the pin has a width less than that of a slot 32 in the blade that extends rearwardly from hole 28. ("Rearwardly" in this description is understood to mean towards the handpiece 13 of the saw 10). Thus, once the narrow portion 31 of the lock pin 26 becomes aligned with the saw blade 12, it is a relatively easy task to simply slide the blade out of slot 24. A more complete discussion of how the blade 12 is locked in head 18 is found in the Applicant's Assignee's U.S. Pat. No. 5,263,972, entitled SURGICAL HANDPIECE CHUCK AND BLADE, issued Nov. 23, 1993, which is incorporated herein by reference.

Extending forward from, and formed integrally with the base 22, saw blade 12 has a main section 36. In the depicted version of the invention, main section 36 has a width greater than that of the base 18 although that is not always be the case. The front edge surface of main section 36 is formed to have teeth 38. Teeth 38 are the cutting elements of the saw blade 12.

From FIGS. 3 and 4 it can be seen that the saw blade 12 of this invention is formed with two leaf springs 42 that are integral with the base 22. The leaf springs 42, which function as cantilever springs, are formed integrally with and located around opposed sides of blade base 22. The leaf springs 42 can be considered to extend into spaces 45 defined by a reduced width section of blade base 22. Each leaf spring 42 extends forward from a position approximately two/thirds along the length of the base, from the rear end of the saw blade 12, towards the main section 36. Each leaf spring 42 has a small, laterally outwardly directed ridge 44 located at the distal end of the base of the spring. When the saw blade 12 is seated in slot 24, ridges 44 abut, have an interference fit, with the adjacent interior side walls 25 of the head 18. More specifically, it can be seen that the total width of the blade between the ridges 44 is slightly more than the width of the blade across the base 22. In some preferred versions of the invention, the width of the blade 12 across the ridges 44 is 0.010 to 0.015 inches (0.25 to 0.38 mm) more than the width of the blade across the section of the blade base 22 located rearwardly of the leaf springs.

From FIG. 4 it can be seen that the saw blade 12 is formed so that there is an L-shaped gap 48 between each leaf spring 42 and the adjacent section of portion of the blade base 22. More specifically, the blade 12 is formed so that the short section of gap 48 extends perpendicularly inward from the side edge of the blade 12 and the elongated section extends rearwardly from the short section so as to form the separation between leaf spring 42 and the rest of the blade base. A small circular through bore 50 is located at the end of the elongated section of gap 48 that is located towards the rear end of the blade. Bore 50 is formed in part as a result of the manufacturing of the blade. The circular cross-sectional profile of bore 50 also serves to reduce the stress that develops when the saw 10 is actuated and the spring 42 pivots relative to the rest of the blade 12.

When saw blade 12 is inserted in slot 24 of saw head 18, the ridges 44 of the leaf springs 42 come into contact with the adjacent side walls 25 of the head to establish an interference fit between the saw blade and the head. When the saw 10 is actuated, saw head 18 engages in oscillating motion to induce like motion in the blade 12. More specifically, the blade 12 is oscillated around point A which is located in center of hole 28. Whenever the saw head 18 changes its direction of motion, as a result of the momentum already developed by the saw blade, the base 22 and main section 36, for a short time, continue to move in the direction that they were previously being urged by the saw head 18. This inertial motion causes the portion of the blade base 22 between the leaf springs 42 to close the gap 48 between the base and the leaf spring 42 towards which the base is moving. However, the saw blade 12 is formed so that the gaps 48 have a width large enough to ensure that the momentum of the blade base 22 will not be sufficient enough to close the gap to zero. In other words, the blade is shaped so that the gap 48 is wide enough to ensure that the momentum of the blade will not cause the portion of the blade base 22 adjacent leaf spring 42 to abut the leaf spring.

The following formulas offer one means for determining the minimum width of the elongated section of gap 48. It should be understood that gap 48 should never be too wide because, during use, it is possible for the blade 12 to impart a reaction force to the saw head 18 that is greater than the inertial momentum for the blade at speed. This reaction force may occur as a result of the blade being employed to perform strenuous cutting or jerking. If this reaction force is significant enough and the gap 48 is relatively wide, the, blade base may be flexed relative to the last springs greater than the material properties of the material forming the spring allow. If the spring 42 are exposed to such flexing, one of both of the spring may permanently bend, yield, or snap off, effectively breaking the blade. Thus, if the gap is designed just larger than necessary to overcome the momen tum change, complete closure of the gap from a greater reaction-type force limits the stress placed upon the spring 42. This essentially eliminates the likelihood of the spring 42 yielding or separating.

The basic formula for determining X, the maximum displacement of the blade base, so one can then determine the width of gap 48 is:

$$X = \frac{F_R l^3}{3EI}$$

Where:
$F_R$ is the positive force of the cantilever spring of leaf spring 42.
l is the length of the spring 42. It should be understood that X is thus calculated for the portion of gap 48 adjacent the end of the spring 42, that is, the end of the spring furthest from the rearward end of the blade base 22.
E is the Youngs Modulus of the material forming saw blade 12.
I is the area moment of the cantilever spring.

The positive force of the leaf spring is calculated according to the formula:

$$F_R = \frac{I_A \alpha}{r_R}$$

Where:
$I_A$ is the mass moment inertia of the saw blade 12 around pivot point A. It being understood that the formula for the mass moment of inertia is a function of the geometry of the blade.
$\alpha$ is the angular acceleration of the blade. This angular acceleration is at its extreme at $\Theta$, the angle of greatest pivot of the blade (the pivot when the blade is fully displaced in one direction by head 18) and zero when the blade is centered (the center of gravity, g, of the blade is aligned with the longitudinal axis of saw 10).
$r_R$ is the moment arm from pivot point A to the point where the resistive force $F_R$ is applied to the spring, the point where the ridge 44 abuts side wall 25.

The area moment for a spring having a rectangular cross sectional profile can be calculated according to the formula:

$$I = \frac{(bh)^3}{12}$$

Where:
b is the depth of the cantilever arm of leaf spring 42, here, the thickness of blade 12.
h is the width across of the leaf spring 42.

The X yielded by the above calculations is the maximum displacement of the blade base 22 owing to the moment of inertia of the blade base. When the spring is formed, the actual width of gap 48 should be slightly larger than this value of X to ensure that, when the blade base 22 closes against the leaf spring 42, there will be an interstitial separation between these two components. For example, it is contemplated that the minimum width of the gap 48 at the point of resistive force should be X+0.001 inches (0.03 mm).

When a saw blade 12 of this invention is inserted into the saw head 18, the leaf springs 42 automatically compress to allow the easy seating of the blade in slot 24. Since the leaf springs 42 flex, significant amounts of force are not required to pull the saw blade 12 from the slot 24 in order to replace the blade.

When the saw 10 with this blade 12 is actuated, the leaf springs 42 remain in continuous contact with the adjacent side walls 25 of the saw head even as the head and blade are oscillated back and forth. Also, as discussed above, when the saw blade 12 engages in inertial movement at the end of a cycle of uni-directional, saw head-induced movement, the blade base 22 comes close to, but does not contact, the adjacent leaf spring 42. Thus, since these two components do not abut, during use of a saw with this blade 12 there is no repetitive metal-to-metal contact due to the inertial motion of the saw blade. Since, this contact is not present, the noise it induces is likewise eliminated.

Thus, this invention provides a saw head and saw blade assembly that is arranged so that the blade can readily be inserted into and removed from the saw blade without the use of any supplemental key or wrench and that does not generate significant noise when engaged in oscillating motion.

It should be recognized that the foregoing description is directed to a specific embodiment of the saw head 18 and saw blade 12 of this invention. Other versions of this invention may vary from what has been described. For example, while in the described version of the invention, the blade base 22 is narrower than the forward extending main section 36, that need not always be the case. In some versions of the invention, the main section may have the same general width or be narrower than the base 22. It should likewise be appreciated that the blade base 22 of this description is shown as having a hole 28 and slot 32 that allow the blade to be securely fastened to one particular saw head 18. In other versions of the invention, the blade may be provided with different openings to allow it to be used with complementary fastening members associated with other saw heads. Also, the blade base 22 and springs 42 may be shaped to facilitate the seating of the blade in different shaped slots or other complementary head openings than the rectangular slot that has been depicted.

Also, the arrangement and design of the springs integral with the saw blade may be different from what has been shown. For instance, there is no requirement that the cantilever spring always have a rectangular cross sectional profile. In some versions of the invention, the spring may have a profile that is square, round, triangular or oblong. Also, it may be desirable to provide some versions of the saw blade of this invention wherein there is only a single leaf spring located on one side of the blade. In these versions of the invention, the blade could be designed so that there is an interference fit between the side of the blade base 22 opposite the side from which the spring extends and the adjacent wall of the saw head. Alternatively, the blade may be designed so that there is a very large separation between the spring-free side of the blade base 22 and the adjacent side wall 25 of the saw head 18. This large separation would facilitate both easy removal/insertion of the saw blade and that the inertial movement of the blade would never be great enough to allow the blade to strike one side wall.

In still in other versions of the invention, it may be desirable to provide one or both sides of the blade with two or more springs. Again, in these versions of the invention, it may be desirable to provide the plural leaf springs on one side of the blade and none, one or a different number of springs on the other side of the blade. Moreover, there is no requirement the all versions of the blade 12 of this invention be provided with the cantilevered leaf springs. Similarly, while in the depicted version of the invention, the leaf springs 42 are formed integrally with the saw blade 12, that need not always be the case. In other versions of the invention, the springs may be separate components that are mounted to the saw blade. For example, it may be desirable to affix coil springs to the blade base. Either the springs or a complementary compression bar would then abut the walls of the saw head 18 defining the slot or opening in which the blade is seated.

Therefore, it is the object of the appended claims to cover all such modification and variations that come within the true spirit and scope of this invention.

The embodiments of the invention in which an exclusive property or privilege is claimed are defined as follows:

1. A surgical saw assembly comprising:
   a handpiece;
   a motor disposed in said handpiece;
   a head attached to said handpiece and connected to said motor to engage in oscillating motion, said head having a opening defined by opposed interior walls in said head;
   a saw blade mounted to said saw head to engage in oscillating motion with said saw head, said saw blade having: a blade base disposed in the opening of said head; a main section that extends forward from said blade base, said main section being formed with teeth; and at least one spring attached to one side of said blade base so as to extend outwardly therefrom so as to abut an adjacent said interior wall of said head when said blade is inserted in the opening; and
   a lock assembly attached to said head for releasably securing said blade base in the opening of said head.

2. The surgical saw assembly of claim 1, wherein said spring of said saw blade is a leaf spring that extends in cantilever form from the side of said blade base from which said leaf spring extends, said leaf spring is formed to have a surface that abuts the surface of said interior wall of said head adjacent said leaf spring and said leaf spring is spaced from said blade base so as to form a gap therebetween.

3. The surgical saw assembly of claim 2, wherein said leaf spring is formed integrally with said blade base.

4. The surgical saw assembly of claim 2, wherein said saw blade is formed to have two said leaf springs, said leaf springs being located on opposed sides of said blade base and said leaf springs abut said opposed interior walls of said saw head.

5. The surgical saw assembly of claim 2, wherein said saw blade is constructed so that the gap between said blade base and said leaf spring is of sufficient width so that inertial motion of the blade generated during oscillating movement of said saw blade will not cause portions of said blade base adjacent said leaf spring to close said gap.

6. The surgical saw assembly of claim 1, wherein said lock assembly secures said blade base to said saw head and releases said blade base from said saw head without supplemental tools.

7. The surgical saw assembly of claim 1, wherein said spring is integrally formed with said blade.

8. The surgical saw assembly of claim 1, wherein said saw blade includes two said springs, each said spring being located on separate sides of said blade base and said springs abut said opposed interior walls of said saw head when said saw blade is inserted in the opening in said head.

9. A saw blade insertable in an opening formed in the head of a powered surgical handpiece, said saw blade comprising:
   a blade base being dimensioned to be inserted in the head opening, said blade base having opposed sides, said blade base having means for receiving a locking element integral with the head;
   at least one spring extending from one side of said blade base, said at least one spring being configured so that, when said blade base is inserted in the head opening, said spring abuts a wall in the head; and
   a main section located forward from said blade base, said main section being formed with a cutting surface.

10. The saw blade of claim 9, wherein said at least one spring is a leaf spring that extends from said blade base and that abuts the wall in the head and, said blade base and said leaf spring are configured to define a gap between said blade base and said leaf spring.

11. The saw blade of claim 10, wherein:
    said blade base has a first section with a first width and a second section located forward from said first section from which said main section extends, said second section having a width less than that of first section; and
    said leaf spring has a base that extends from said first section of said blade base that is located along a side of said second section of said blade base that has a width and a ridge that is located at the end of said leaf spring base adjacent said second section of said blade base said ridge has a width greater than that of said leaf spring base so that said ridge abuts the wall in the head.

12. The saw blade of claim 10, wherein said blade base has two said leaf springs, and said leaf springs extend from the opposed sides of said blade base.

13. The saw blade of claim 10, wherein said leaf spring is formed integrally with said blade base.

14. A saw blade for insertion into the head of a powered surgical handpiece, said saw blade comprising:
    a blade base dimensioned to be inserted into the head, said blade base having opposed sides;
    spring assemblies attached to the opposed sides of said blade base, each said spring assembly being configured to abut an adjacent interior wall of the head to prevent the side of the blade base from which said spring assembly extends from contacting the interior wall;
    a main body that extends forward from said blade base, said main body being formed to have a cutting surface.

15. The saw blade of claim 14, wherein each said spring assembly includes a leaf spring.

16. The saw blade of claim 15, wherein each said leaf spring has a base that extends from said blade base towards said main body, said spring base having a width, and a ridge section located at a free end of said spring base, said ridge section having a width greater than the width of the spring base.

17. The saw blade of claim 14, wherein said spring assemblies are formed integrally-with said blade base.

18. The saw blade of claim 14, wherein said blade base is further provided with means for receiving locking members to hold said blade base in the head.

19. A saw blade for insertion into a slot of an oscillating head of a surgical tool, said saw blade including:
    a blade base having opposed sides and a first section with a width between the sides less than a width of the slot so that said blade base is positionable in said slot and a second section located adjacent said first section that has a width less than the width of the first section;
    two leaf springs, each said leaf spring extending from a separate side of said blade base first section so as to extend into a space adjacent the side of said blade base second section and dimensioned to form a gap between said leaf spring and the adjacent side of said blade base second section, wherein said leaf springs are so formed that said leaf springs and said blade base second section has a width greater than the width of said blade base first section and said gap is dimensioned so that inertial movement of said blade base second section will not cause closure of said gap; and a main section formed contiguously with said blade base second section, said main section being formed with a cutting surface.

20. The saw blade of claim 19, wherein said leaf springs are formed integrally with said blade base.

21. The saw blade of claim 19, wherein said blade base is further provided with means for receiving locking members to hold said blade base in the head slot.

22. A surgical saw assembly comprising:

a handpiece;

a motor disposed in said handpiece;

a head attached to said handpiece and connected to said motor to engage in a oscillating motion, said head having a slot defined by interior walls in said head, said slot having a width;

a saw blade mounted to said saw head to engage in reciprocal motion with said saw head, said saw blade having:

a blade base disposed in the slot of said head, said blade base having opposed sides located adjacent the interior walls in said head and a width less than the width of the slot;

oppose d spring members that are integrally formed with said blade base, each said spring member extending outwardly from one side of said blade base abutting an adjacent one of the interior walls of said head; and a main section that extends forward from said blade base, said main section being formed with cutting surface; and a lock assembly attached to said head for releasably securing said blade base in the slot of said head.

23. The surgical saw assembly of claim 22, wherein each said spring member is a leaf spring is formed to have: a base that extends from said blade base, and the width across said spring bases is substantially equal to the width across said blade base; and a ridge section that extends from a free end of said spring base, said spring member being formed so that said ridge section abuts the adjacent interior wall of said head.

* * * * *